United States Patent [19]

Walsh

[11] Patent Number: 4,898,852
[45] Date of Patent: Feb. 6, 1990

[54] CYCLOPOLGALCTURONIC ACID COMPOSITION AND TREATMENT

[76] Inventor: William E. Walsh, 990 Lydia Dr., Roseville, Minn. 55113

[21] Appl. No.: 57,166

[22] Filed: Jun. 2, 1987

[51] Int. Cl.$^4$ ............................................. A61K 7/00
[52] U.S. Cl. ...................................... 514/54; 514/58; 514/859; 536/103; 424/195.1
[58] Field of Search ........................... 514/54, 58, 859; 536/103; 424/195.1

[56] References Cited

U.S. PATENT DOCUMENTS

| | | | |
|---|---|---|---|
| 4,247,535 | 1/1981 | Lewis et al. | 514/58 |
| 4,306,021 | 12/1987 | Dolak et al. | 435/128 |
| 4,569,839 | 2/1986 | Grollier et al. | 424/195.1 |
| 4,634,436 | 1/1987 | La Tour | 424/195.1 |
| 4,734,403 | 3/1988 | O'Hinterland et al. | 514/54 |

FOREIGN PATENT DOCUMENTS

| | | | |
|---|---|---|---|
| 1104578 | 7/1981 | Canada | 260/429.4 |
| 2116036 | 9/1983 | United Kingdom . | |

OTHER PUBLICATIONS

S. Joveva et al., Chemical Abstracts Mar. 3 (1986), vol. 104, p. 594, abstract 104:67794w.
B. Casu et al., Carbohydrate Research, 63, 13–27 (1978).
Tjan et al., Carbohydrate Research, 34, 15–32 (1974).
Daniel W. Armstrong and Weiyong Li, Optimization of Liquid Chromatographic Separations on Cyclodextrin–Bonded Phases, Chromatography, Mar. 1987, pp. 43–47.
Federal Register, vol. 50, No. 10, Tuesday, January 15, 1985, proposed Rules, 21 CRF Part 333, Part V, Department of Health and Human Services, Food and Drug Administration.
Henry H. Roenigk, Jr., M.D., Retinoids, Department of Dermatology, Northwestern University Medical School, Chicago, Il, Cutis vol. 39, Apr. 1987, pp. 301–305.
Kirk–Othmer Encyclopedia of Chemical Technology, vol. 15, 2nd Edition (1968), pp. 112–132.
Aldrich Chemical Company, Inc. Technical Bulletin, Aldrich Fine Chemicals, pp. 373–374.
Markkanen et al., "Antiherpetic Agent from Juniper Tree (Juniperus communis), Its Purification, Identification, and Testing in Primary human Amnion Cell Cultures," Drugs Exptl. Clin. Res. VII(5) 691–697 (1981).
Translation of S. Joveva et al., "Feasibility of Using Thin–Layer Chromatography to Determine Carbohydrates in the Juniper Berry," (Chemical Abstracts 104:67794W) No. 9, Mar. 3, 1986.

Primary Examiner—Ronald W. Griffin
Attorney, Agent, or Firm—Merchant, Gould, Smith, Edell, Welter & Schmidt

[57] ABSTRACT

Novel cyclopolyglycuronic acid compounds which are useful in the treatment of symptom relief in human disease including acne, blackheads and other facial lesions.

15 Claims, No Drawings

CYCLOPOLGALCTURONIC ACID COMPOSITION AND TREATMENT

FIELD OF THE INVENTION

The invention relates to novel pharmaceutical compositions and their use in treating or reducing the symptoms of human disease. More particularly the invention relates to novel pharmaceutical compositions that can be used in the form of a topical cream or ointment, in a pill or capsule format, in an injection concentrate or solution, in a composition that can be nebulized or in compositions in the form of a suppository. More particularly the invention relates to a novel pharmaceutical composition that has shown particular value in the treatment of acne and other related dermal lesions.

BACKGROUND OF THE INVENTION

Polysaccharide compounds in general have been used in many pharmaceutical applications, typically as structural materials (cellulosics) and as thickeners or diluents (starches, sugars, gums, etc.). Certain specialized carbohydrate-containing molecules are known to be antibiotic, for example derivatives of 2-aminogalactose and others, while cyclic polydextrans are known having 6, 7 and 8 glucose units. Such compounds are known as an inhibitor of pullulanase, an enzyme known to cleave the alpha(1→6) saccharide bonds of amylo-pectin, are known to form clathrates and are known to be active as chromatography supports. However, to the best of our knowledge cyclodextrans and related compounds are not known as a class of active pharmacutical treatment compositions.

Acne (acne vulgarous) is a chronic disorder of the skin generally confined to face, chest and back. Primary acne lesions appear as horny plugs (blackheads) which later can develop into pink papules, pustules, or nodules. The nodules can be tender, acute, localized collections of pus deep in the dermis. Large pustular lesions may develop and break down adjacent tissues to form lakes of pus, sinuses and characteristically pitted scars. Tests have shown that heredity is a major predisposing factor in the disease which is described as polygenic (some defects are caused by a group of genes) and is difficult to clearly delineate heredity effects. Acne typically has a puberty or post-puberty onset wherein pilosebaceous units enlarge and produce sebum. Acne can occur when an excess of sebum is produced or when the folicular openings are too small to permit the escape of increased sebum flow; or under both conditions. The duration of acne vulgarous after onset is highly variable and can persist into the fourth decade of life but typically peaks during the teen years and typically terminates in the third decade of life.

After years of research a number of treatments have been proposed including benzoyl peroxide, salyclic acid, sulfur, retinoids (vitamin A derivatives), repeated washings to reduce the population of skin microflora, antiseborrheic shampoos, and moderate exposure to the sun which have been shown to be somewhat beneficial in certain individuals. In severe cases, broad spectrum systemic antibiotics have been effective in treating inflammatory acne, preferably tetracycline is used. Lastly, in many cases anti-inflammatory drugs have reduced the severity of the acne outbreaks.

Clearly a substantial need exists for effective treatments of acne and related skin disorders that can reduce or alleviate the unsightly aspect of the skin disorder.

BRIEF DISCUSSION OF THE INVENTION

I have discovered a novel class of compounds, namely the cyclic polymers having repeating units derived from six carbon furanose or pyranose saccharic acids having at least four saccharic acid residues.

We have also found that the administration of one or more of the cyclopolysaccharic acid compositions of the invention to human patients having acne lesions can provide some relief of symptoms including removal of blackheads, reduction in size of acne lesions, and improved rates of healing. We also believe that the compounds of the invention can be useful in the treatment or reduction of symptoms in a variety of human diseases other than dermal disease involving a variety of organs and systemic disorders.

DETAILED DISCUSSION OF THE INVENTION

The cyclopolysaccharic acids of this invention can be obtained from natural sources or can be synthesized using known chemical principles. The pure or semipure preparations of the cyclic cyclopolysaccharic acid compounds can be applied to subjects in a variety of formats including as a topical cream or ointment, as a pill or capsule, as an injection solution or concentrate thereof, as a nebulized aerosol or in the form of a suppository.

We have found that the cyclopolysaccharic acid compound can be obtained by fractionation of plant sources. We have found that the compounds of the invention occur naturally in relatively high concentration in juniper berries. If synthesis of pure compounds is desired, the class of polysaccharic acids can be prepared by one of two synthetic routes.

The term "saccharic acid" in this invention means a mono saccharide in a furanose or pyranose ring structure having a carboxyl group, preferably the 6-carbon atom is in the form of a carboxyl group. Saccharic acids that can be included in the cyclic polymers of the invention include α-D-glucopyranosic acid, α-D-mannopyranosic acid, α-D-fructofuranosic, other similar acids and mixtures thereof, said acids having the following formulae:

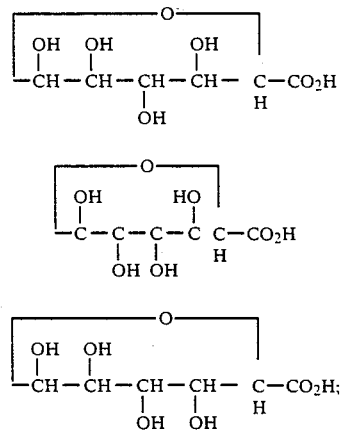

and

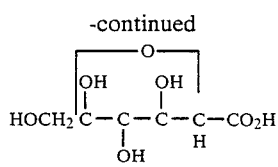

Such polymers are typically formed by (1→4), (2→4), (1→3), (2→3), linkages between the monosaccharic acid units to form the cyclic polymer.

Synthetic Route No. 1

In a first synthetic route, members of the class of cyclopolysaccharic acids can be prepared by obtaining an oligosaccharide of an appropriate number of units or a mixture of various oligosaccharides and converting the linear oligosaccharide into a cyclic oligosaccharide or polysaccharide. When cyclized the 6-carbon (typically a —$CH_2OH$) of each unit can be oxidized using known reaction reaction schemes to a carboxyl (—$CO_2H$) functionality. Such reactions are well known to the skilled synthetic organic chemist. In both the cyclyzing reaction the 2, 3 and 6 free hydroxyl groups of the oligosaccharide can be blocked using a variety of blocking agents such as acetyl groups and others. During the oxidation step, the 6 carbon typically is unprotected during the reaction while the 2 and 3 hydroxyls can be protected with a functional group such as acetyl or others. Oxidation of the primary hydroxyl (—$CH_2OH$) may be accomplished without blocking secondary hydroxyls (at 2 carbon or 3 carbon sties) under appropriate reaction conditions. Alternatively, the oligosaccharide composition can first be oxidized in each of its 6 carbon positions converting the oligosaccharide to a linear polysaccharic acid. During such oxidation steps the 2 and 3 carbon hydroxyl groups are typically protected from oxidation by blocking groups such as acetyl and others. Once oxidized to a linear polygalacturonic acid, the linear polymer can be cyclized using known reaction schemes to a cyclic polygalacturonic acid. After cyclization and oxidation is complete, the blocking groups remaining on the polycyclo acid unit can be removed with known techniques. Again under appropriate mild conditions oxidation may be accomplished without blocking the 2 or 3 hydroxyl groups.

The cyclization step is preferably conducted by converting the free 1 carbon of the galacturonic acid oligosaccharide to a galactosyl halide such as chloride and/or bromide and in dilute solution permitting the galactocyl halide to react with the terminal 4-hydroxyl group in the oligosaccharide molecule. Other cyclization reactions can be used such as the use of a diacid functional molecule to react with the free 1 and 4 terminal hydroxyl groups in the oligosaccharic molecule creating the linked cyclized poly form.

The preferred cyclopolysaccharic acid comprises a molecule made of a 6 carbon cyclopyranose saccharic acid. The most preferred compound comprises a molecule of the formulae:

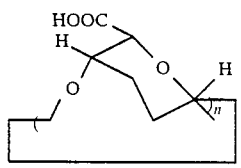

wherein n is greater than 4 and preferably n is an integer of 5 to 10. The most preferred compound is a cyclopolygalacturonic acid compounds of the invention comprise a cyclobeta-D-(+) polygalacturonic acid having 5 or 8 galacturonic acid units of the formula:

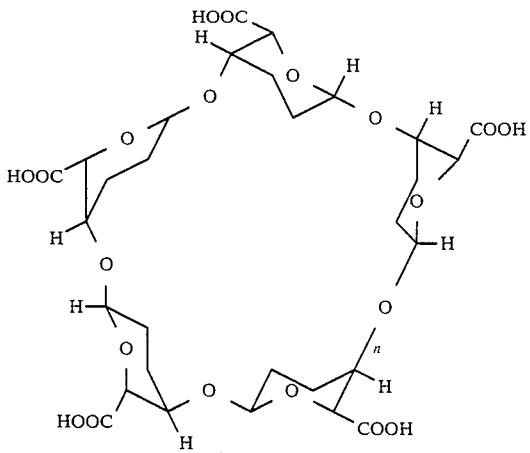

wherein n=1 to 4.

The most preferred cyclopolygalacturonic acid compositions of the invention are preferably obtained from natural juniper berry sources through a boiling water extraction from the natural source with subsequent purification of the material.

In somewhat greater detail, the preferred compounds of the invention can be obtained from crushed presoaked berries using a 24-hour boiling water Soxhlet extraction procedure utilizing 1200 milliliters of water and 200 grams of the crushed berries. Typically the initial extraction procedure results in 1 to 2 grams of semipurified material containing the active cyclopolygalacturonic acid compounds. At least a 24-hour extraction appears to be required to fully extract active material from the source. Further, the presoaking period appears to permit natural enzyme action which appears to make the cyclopolygalacturonic acid compounds more available to boiling water extraction. After the aqueous extraction is complete, an acidified (pH 3-5) aqueous preparation of the compound is extracted with moderately polar organic solvents to remove small amounts of natural fats and oils in the aqueous extract. The fat-free aqueous concentrate is separated into components using a chromatographic component separation. We have found that reverse-phase chromatography provides purest active material. In this technique constituents are separated according to their relative hydrophobicity (or polarity) and tested for activity. The reverse phase chromatography enables the ready separation of simple sugars from the aqueous solution by elution while retaining the materials of mixed polarity including the cyclopolygalacturonic acids. A later elution with a methanol/water cosolvent material (typically greater than 40 volume-% methanol) successfully elutes the cyclopolygalacturonic acid compositions. After elution, active material can be precipitated by addition of methanol to a concentrated aqueous extract. After precipitation subsequent reverse-phase chromatography can be applied to reduce the free monocarbohydrate or oligosaccharide content of the cyclopolygalacturonic acid fractions. It is clear that using these procedures relatively purified cyclopolygalacturonic acid compounds have been obtained in view of the compound characterization that follows.

The molecular structure assigned to the active class of compounds of the invention has been obtained using spectroscopic analysis, elemental analysis, chemical enzyme and enzymatic modification, interpretation of chromatographic behavior, and observation of the effects of the composition on the surface tension of aqueous solutions. I have concluded that the biologically active molecule is an acidic polysaccharide, related to pectin (a linear polygalacturonic acid). No evidence of active fatty acids or hydrocarbon glycosides (i.e. saponin or otherwise), or a nitrogencontaining material (an amino acid or an amino sugar) is shown. Nuclear magnetic resonance spectroscopy, both proton and carbon ($^1$H- and $^{13}$C-spectroscopy; see FIGS. 1 and 2) support a carbohydrate structure with no aliphatic or aromatic hydrocarbon substituents. Infrared analysis (FIG. 3) supports the polyhydroxy structure. Elemental analysis shows that elements other than carbon, hydrogen and oxygen appear to be absent. From acid base reactions the material appears to have an acidic functionality and through reaction with commercial pectinase preparation the composition appears to comprise a polygalacturonic acid sequence. A cyclic structure is suggested by its tendency to associate with a variety of compounds and surfaces.

The presence of carboxylate groups on the molecule suggests the possibility that the compound may be absorbed directly in the stomach (at low pH, suppression of dissociation of the proton maximizes direct absorption into the lining of the stomach). This characteristic would be advantageous in that effective levels in blood could be achieved through oral administration instead of cumbersome intravenous injection in humans.

Application and Dosage

Cyclopolygalacturonic acids have been shown to possess anti-acne and antifacial lesion activity in human subjects. The effective dosage of the cyclopolygalacturonic acids is about 0.001 to 50 milligrams, preferably about 0.01 to 5 milligrams, per kilogram of body weight and is applicable to human subjects in topical form, in lotions or creams, in oral dosage in pharmaceutically acceptable carriers in the form of pills and capsules, in intravenous or intramuscular or subcutaneous injection from aqueous solution, or a suspension that is nonpyrogenic and pharmaceutically acceptable that can be made from pharmaceutical liquid or solid concentrates, in the form of nebulized aqueous dispersions and in the form of suppositories. The cyclopolygalacturonic acid compounds of the invention can be combined with other topical or systemic treatment compounds to provide a "synergistic" treatment regimen.

With respect to oral treatment by capsule or pill, the presence of carboxylate groups on the molecule suggests the possibility that the compound may be absorbed from the stomach at low pH with the inherent suppression of proton dissociation and increased absorbability in the stomach. This characteristic would be advantageous in that effective blood levels could be achieved by oral administration instead of more cumbersome injection treatments. In a pill or capsule form, the composition of the invention should be administered in a dosage regimen of about 0.01 to 5 milligrams of active compound per kilogram of body weight.

Tablet, capsule, or pill treatment formats of the compositions of the invention can contain inert fillers, enabling the manufacturer to readily dispense the compositions in active form which inert fillers include lactose, mannitol, sucrose, calcium sulfate, calcium phosphate, microcrystalline cellulose gums, methyl cellulose, cornstarch, alginic acid, stearic acid, magnesium stearate, carbowax, and others.

The compounds of the invention can also be applied topically in a pharmaceutically acceptable ointment or cream. The concentration of the active compositions, of the invention in a topical preparation is about 0.1 to 10% based on the topical preparation. Topical ointments or creams are typically blends of the active compositions in a silicone gel or in a petroleum or refined petroleum base. The base may contain other additives such as zinc oxide, lanolin, waxes, starches or other viscosity modifiers. Creams are typically semi-solid emulsions of either the water in oil or oil in water types or a polysilicone gel.

For intravenous, intramuscular, and subcutaneous injection, the composition of the invention can be formulated in pharmaceutically acceptable injection solutions wherein the active composition is present at a concentration of about 10 to 5000 milligrams per liter. Dosages should be applied to human subjects such that about 0.01 to 5 milligrams per kilogram of body weight is applied per treatment. Treatments can be repeated to maintain an effective concentration of the active compositions of the invention in the bloodstream.

Parenteral products which are injectable are typically aqueous based solutions or suspensions of the active composition. Typically nonpyrogenic water is used. The products of the invention can be in a liquid concentrate or dry powder that is dissolved or suspended in aqueous medium for injection. Typically injectable compositions contain bacteriostatic agents and can be included with aqueous vehicles such as isotonic sodium chloride, ringers injection solution, dextrose injection solution, dextrose and sodium chloride injection solution, and lactated ringers injections solutions which are isotonic with respect to blood chemistry.

The following Examples are provided to support an understanding of the invention and to include a best mode.

EXAMPLE 1

205 grams of juniper berries were crushed and soaked in distilled water for 2 weeks. The soaking water was removed and the crushed berries were placed in a large scale Soxhlet extraction apparatus (said apparatus containing a condenser, extractor and a heated round bottom flask) containing 1200 milliliters of distilled water. Heating was initiated and a boiling water extraction continued for 24 hours. The aqueous Soxhlet extract was removed from the Soxhlet extractor and extracted twice with ethyl acetate (2400 milliliters and 1600 milliliters aliquots). The organic layer was separated and discarded. The aqueous phase was placed in a 4 liter Erlenmeyer flask and into the aqueous composition was placed 3000 milliliters of methanol. A precipitate was formed which was filtered. The methanolic solution was evaporated. The total material obtained in the filtrate and the residue after evaporation totalled 14.72 grams. The filtrate and residue was subject to carbohydrate thin layer chromatography which revealed that both compositions were chemically similar having components at RF of about 0.55 and baseline residue.

A reverse-phase chromatography column was packed with 50 grams of $C_{18}$ coated support. The combined samples were placed on the column and washed with about 250 milliliters of water. The water collection was fraction 1. The column was washed with a 50 volume-% methanol/water solution and the elution was collected in 5 equal fractions (fractions 2-6) totalling approximately 900 milliliters. Lastly, the column was washed with 100% methanol, collected in 4 fractions (fractions 7-10) totalling 600 milliliters. Fraction 3 appeared to have the maximum treatment activity and the minimum surface tension in aqueous solution of 50 milligrams of the material and 50 milliliters of water. The surface tension was about 50.6 dynes per centimeter. Unconverted distilled water measured 60.5 dynes/cm.

| Elemental Analyses (M-H-W Laboratories, Phoenix, Arizona) | | |
| --- | --- | --- |
| Element | Percent Calculated | Percent Found |
| C | 37.1 | 46 |
| H | 5.2 | 5.7 |
| O | 57.7 | 48.3 |

The compound was soluble in water, insoluble in methanol, and insoluble in ethyl acetate and chloroform. Treatment of the composition with pectinase changes its properties, implying a polygalacturonic acid sequence structure.

The infrared spectrum of the composition gave absorbences of the following wave numbers ($cm^{-1}$): 3400S, 2930M, 2110W, 1730M, 1620M, 1510M, 3810M, 1250M, 1150M, 1110M, 1040S, 805M, 700W, 6150W.

The $^1H$-NMR (proton magnetic resonance spectrum) of the polycyclogalacturonic acid compounds at 300 Megahertz is shown in FIG. 1. The proton spectrum was observed on a NICOLET magnetic resonance spectrophotometer on a solution (CA 0.5 milliliters of an approximate concentration of 50 milligrams per milliliters). Of the sample of the compound in a denatured water ($D_2O$) solvent. The spectrum was calibrated against an internal standard: DDS [3-(trimethylsilyl)-1-propane sulfonic acid, sodium salt)] and frequencies recorded in parts per million downfield from the standard.

The $^{13}C$-NMR spectrum of the compounds of the invention are shown in FIG. 2 of the Drawings. The $^{13}C$-NMR spectrum was observed on a Brooker UM-250 spectrometer on a solution (about 0.5 milliliters of an approximately 50 milligrams per milliliter solution of the sample of the compound in a $D_2O$:solvent). The spectrum was calibrated against an internal DDS standard and frequencies were recorded in parts per million downfield from the standard.

We believe that the compounds of this invention can be useful in treating the following conditions: hyaline membrane disease in infants for the purpose of increasing oxygen transfer over the hyaline membrane in newborns and premature infants; cystic fibrosis to loosen up the thick, heavy mucous that forms in the luns; asthma; chronic bronchitis; chronic obstructive lung disease or emphysema; serious otitis media and sinus congestion and pneumonia.

Additionally, dermal conditions may benefit from this preparation for improving the softness and wrinkling of normal skin, reduction in the oiliness of skin, improvement in seborrhea, psoriasis and eczema.

The compositions of the invention appear to be attracted to surface characteristics. As a result aqueous solutions of the composition tend to lose potency as the active ingredient tends to plate onto the surfaces of containers. Most successful topical preparations appear to be in the form of a zinc oxide preparation in a petroleum base. It appears that the zinc oxide cooperates with the polycyclogalacturonic acid composition to prevent separation and surface association.

The active compositions which have been tested comprise 500 milligrams of the cyclopolygalacturonic acid compounds formed in Example 1 in 99.5 grams of an ointment base containing 25 wt-% zinc oxide, 25 wt-% starch and 50 wt-% white petroleum.

CASE STUDIES

Case A

Case A is a 10 year old boy who has had blackheads on his nose for the past year. They are impossible to remove by hard scrubbing or by trying to press out. The substance was applied to his nose once daily in a zinc oxide vehicle. After three weeks the blackheads began to loosen and many were expressed spontaneously. At the fourth week the remainder, about half, were expressed manually. Little pressure was necessary to remove the remaining blackheads.

Case B

Case B is a 13 year old boy with three years of acne vulgarous. Blackheads and pustules covered his forehead, cheeks and chin. The substance was applied topically in a zinc oxide vehicle and within a week ne pustules no longer erupted. By the third week most of the pustules had discharged themselves and new blackheads were not forming, old blackheads were beginning to spontaneously erupt. By the fourth week there were few pustules and blackheads and most of the original pustules had disappeared or decreased to non-elevated red areas from which they would be expected to eventually disappear altogether.

Patient B noticed that when he was on treatment his skin felt smoother and that the thick oil on his skin changes to a very light oil that was easily removed by washing.

Case C

Case C is a 15 year old boy with severe acne over the past three years. Previous treatment including topical agents and tetracycline were not effective in controlling the acne. Pustules and blackheads were found over his face and on his shoulders and back.

The substance in zinc oxide was administered to the face and back. The first change noticed by the patient was a decrease in the greasy feeling of his face and a softening of the skin of the face and shoulders. Following this, no new pustules erupted nor new blackheads formed. By the third week, blackheads were beginning to erupt spontaneously and there was a great decrease in many of the earlier pustules. Many of the old pustules were flat and by the fourth week the redness was beginning to leave the area where the old pustules were.

Case D

Case D is an 18 year old boy with severe acne of four or five years duration. Pustules and blackheads covered his face and back. Previous treatment with antibiotics and topical ointments has resulted in limited control.

The use of the substance in zinc oxide caused a change in the greasy feeling of his skin within the first week and a feeling of smoothness. During this period no new pustules erupted and no new blackheads formed. By the third week blackheads were beginning to erupt spontaneously and by the fourth week they were easy to express. During the third and fourth week the pustules had decreased in size and many of the old ones were flat and the red color in them was decreasing and vanishing.

Case E

Case E is a 49 year old male with mild acne which had been present since childhood. During childhood it had been severe. There were small blackheads on the face and papular eruptions on the back of the neck and back.

The substance in zinc oxide was applied topically. During the first week a marked change in the sensation of the skin was felt with the skin becoming much smoother and the feeling of heavy oiliness changing to a light oily feeling that was easily removed with washing. By the third week many of the blackheads were beginning to erupt spontaneously and others were expressed easily. By the fourth week the papular eruptions at the back of the neck had subsided and the face was clear of blackheads.

The above data, spectrum, Example and case studies provide a clear understanding of the efficacy, utility, and identity of the compounds of the invention. However, since many embodiments of the invention can be made without departing from the spirit and scope of the invention, the invention resides in the claims hereinafter appended.

I claim:

1. A substantially pure cyclopoly-beta-D+-galacturonic acid compound of the formula:

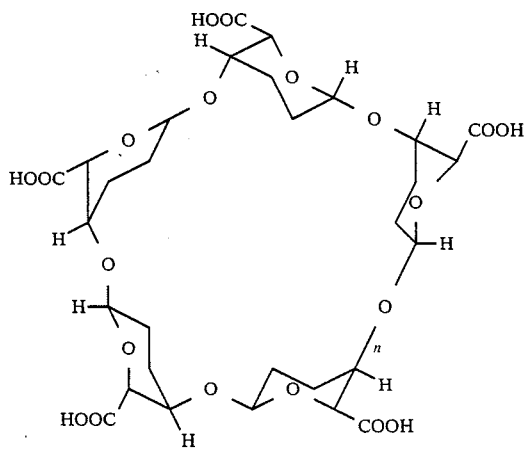

and pharmaceutically acceptable salts thereof, wherein n is an integer of 1 to 10.

2. A viscous liquid topical application comprising a major proportion of a pharmaceutically acceptable liquid base and about 0.1 to 10 wt-% of the cyclogalacturonic acid compound of claim 1.

3. An oral treatment composition comprising a capsule or tablet comprising a major proportion of a pharmaceutically acceptable solid diluent and about 0.1 to 10 wt-% of the cyclogalacturonic acid compound of claim 1.

4. A parenteral treatment composition comprising a major proportion of a liquid diluent and about 0.001 to 50 wt-% of a cyclogalacturonic acid compound of claim 1.

5. A parenteral composition comprising a major proportion of an injectable, nonpyrogenic liquid vehicle and 0.001 to 0.5 wt-% of a cyclogalacturonic acid compound of claim 1.

6. The parenteral composition of claim 5 wherein the liquid nonpyrogenic diluent comprises water.

7. A method for the treatment of acne vulgarous which comprises applying to a human subject an effective amount of the cyclogalacturonic acid compound of claim 1 to reduce the symptoms of acne.

8. The process of claim 7 wherein the cyclogalacturonic acid compound is applied in the form of a topical liquid.

9. A cyclogalacturonic acid composition comprising a cyclic polymer having repeating units derived from a monogalacturonic acid in a furanose or pyranose ring structure.

10. The cyclopolygalacturonic acid composition of claim 9 wherein the polymer is a copolymer and contains units derived from a source other than a saccharic acid.

11. The cyclopolygalacturonic acid composition of claim 9 wherein the linkages between saccharic acid units are (1→4).

12. A process for recovering a substantially pure cyclopolygalacturonic acid compound from a plant source which comprises:
 (a) extracting crushed juniper berries with an aqueous extraction vehicle to produce an extraction liquor;
 (b) removing neutral lipids from the extraction liquor with an appropriate hydrocarbon solvent;
 (c) removing mono and disaccharides from the extraction liquor; and
 (d) recovering a solid cyclopolygalacturonic acid compound.

13. A process for recovering a substantially pure active composition useful in the treatment of acne vulgarous which comprises:
 (a) contacting crushed juniper berries with an aqueous extraction vehicle to produce an extraction liquor;
 (b) acidifying the extraction liquor to form an acidified extract having a pH less than 7; and
 (c) combining the acidified extract with a pharmaceutically acceptable carrier.

14. The method of claim 13 wherein the pharmaceutically acceptable carrier is a topical carrier.

15. A product of the method of claim 13.

* * * * *